United States Patent [19]

Koike et al.

[11] Patent Number: 5,041,265

[45] Date of Patent: Aug. 20, 1991

[54] HYDROGEN GAS ANALYZER WITH IMPROVED DELIVERY SYSTEM

[75] Inventors: Hideki Koike; Kenji Takeda; Kimio Miyatake, all of Miyanohigashi, Japan

[73] Assignee: Horiba, Ltd., Kyoto, Japan

[21] Appl. No.: 546,043

[22] Filed: Jun. 28, 1990

[30] Foreign Application Priority Data

Jul. 12, 1989 [JP] Japan ............................ 1-81897[U]

[51] Int. Cl.⁵ .......................................... G01N 31/12
[52] U.S. Cl. ...................................... 422/94; 422/83; 73/23.2; 73/23.31; 73/23.32
[58] Field of Search .............. 422/94, 83; 73/23.2, 73/23.31, 23.32

[56] References Cited

U.S. PATENT DOCUMENTS

| | | | |
|---|---|---|---|
| 3,593,023 | 7/1971 | Dodson et al. | 422/94 X |
| 3,888,109 | 6/1975 | Sharki et al. | 73/23.2 |
| 4,128,458 | 12/1978 | Obiaya | 422/94 X |
| 4,622,009 | 11/1986 | Bredeweg | 73/23.31 X |

Primary Examiner—Robert J. Warden
Assistant Examiner—Stephanie Blythe
Attorney, Agent, or Firm—Joseph W. Price

[57] ABSTRACT

A hydrogen gas analyzer having an improved delivery system is provided wherein a plurality of branched passageways can supply a sample cell and an additive fuel to a combustion chamber. Cutoff valves can be activated to control the flow rates through the respective passageways so that when the concentration of hydrogen in the sample gas is high, the flow rate from the additive fuel will be reduced, and when the concentration of hydrogen is low, the flow rate of the sample gas is reduced.

12 Claims, 1 Drawing Sheet

HYDROGEN GAS ANALYZER WITH IMPROVED DELIVERY SYSTEM

BACKGROUND OF THE INVENTION

1. Field of the Invention

The present invention relates to a hydrogen gas analyzer for determining the concentration of hydrogen gas contained in a sample and, more particularly, to a hydrogen gas analyzer having an improved delivery or feed system wherein a sample gas and an additive fuel gas are introduced into a catalytic combustion tank and combusted to measure the water byproduct produced.

2. Description of Related Art

Apparatus for measuring the concentration of hydrogen ($H_2$) gas contained in a sample, such as combustion exhaust gas, is known in the prior art. The manner in which the concentration of gas is measured through an analysis of the byproduct of water output from a combustion tank is also known.

Referring to FIG. 2, a schematic illustration of a prior art hydrogen gas analyzer is disclosed. A catalytic combustion tank 1 containing an oxidizing catalyst agent is connected to a sample gas supply passage 4 and an additive or supplemental fuel gas supply passage 5, both being provided with restrictive capillaries 2 and 3 for regulating the respective flow rates. A junction or Y-connector 7 can be used for connecting the respective gas supply passageway 4 and supplemental fuel gas supply passageway 5 to the catalytic tank 1. A sample gas SG, such as a combustion exhaust gas, and a supplemental fuel gas J, such as air or oxygen, can be introduced into the catalytic tank 1 to combust the sample gas SG and produce a resultant byproduct of water ($H_2O$) in the resultant output gas G. The amount of water can be quantitatively determined by means of a water meter 6, which is known in the art, to measure the concentration of the hydrogen gas contained in the combustion exhaust gas. The water meter 6 can comprise, for example, an infrared gas analyzer.

A problem can occur if the combustibility of the additive fuel deteriorates, since $H_2$ (hydrogen), CO (carbon monoxide), and HC (hydrocarbons) are also frequently contained in the combustion exhaust gas produced by the combustion of petroleum refinery fuels. If a significant amount of these other components are contained in the sample gas, it is possible to generate a byproduct of $H_2O$ through the combustion of the HC coexisting in the sample gas SG. As a result, a subsequent measurement by a hydrogen gas analyzer can produce a quantitative determination of $H_2O$ by means of the water meter 6 that would not only include $H_2O$ resulting from combustion of $H_2$, but also $H_2O$ resulting from the combustion of the HC. As a result, the measurement accuracy can be directly affected. One suggested solution to this problem is based on the fact that $H_2$ is highly combustible and can be combusted at temperatures lower than HC. Accordingly, an attempt is made to lower the temperature of the catalytic tank 1 so it would be difficult to combust the HC components.

An additional problem, however, can occur because other components in the sample gas SG, such as CO, can also be burned together with the $H_2$ so that the combustion heat, proportional to the concentration of CO and $H_2$ generated by their combustion, can effectively raise the temperature of the catalytic tank 1 to the point that the HC components can also be combusted. As a result, the accuracy of the measurement of the water meter 6 is affected.

There have been suggestions that the sample gas SG should be diluted with an assistant or additive fuel gas J, but this can have the effect of reducing the concentrations of $H_2$ and CO in the sample gas SG so that the combustion heat produced by their combustion is reduced and the temperature rise of the catalytic tank 1 is reduced. In these circumstances, the combustion of the HC components are minimized. A problem still exists, however, in that the signal-to-noise (S/N) ratio in the water meter 6 is further deteriorated due to the dilution of the sample gas SG. Accordingly, the accuracy of the measurement is further reduced.

Accordingly, there is still a desire in the prior art to try to improve the analysis of a sample gas in which the concentration of hydrogen is desired to be determined.

SUMMARY OF THE INVENTION

The present invention has been accomplished in response to the requirements of the prior art that have not been heretofore addressed. It is an object of the present invention to provide an improved hydrogen gas analyzer capable of conducting a highly accurate measurement without being adversely influenced by other components such as HC in the sample gas.

In order to achieve the above-described object, when the concentration of the hydrogen gas in a sample gas introduced into a catalytic tank combustion is comparatively high, the dilution ratio of the sample gas with the assistant fuel gas is increased, while, when the concentration of hydrogen is relatively low, the same dilution ratio is reduced. A source of an additive fuel and a source of a sample gas are connected to a combustion tank through a delivery system of, respectively, through two pairs of passageways of predetermined flow rates. A controller can control the flow rates of the first passageways relative to the second passageways, whereby when the concentration of hydrogen in the sample gas is high, the flow rates of the first passageways are reduced, and when the concentration of hydrogen in the sample gas is relatively low, the flow rates of the second passageways connected to the sample gas are lowered. Accordingly, when the concentration of hydrogen is comparatively high, the dilution ratio of the sample gas with the assistant fuel gas is increased, so that the concentrations of hydrogen and CO in the sample gas are reduced. Thus, the combustion heat that can be generated by their combustion is also reduced to reduce any rise in temperature in the catalytic combustion tank. This will minimize the combustion of HC components. With this arrangement, the S/N ratio in the water meter is not reduced, and accordingly the sensitivity of the measurement is not only reduced, but a highly accurate measurement can be conducted.

When the concentration of hydrogen in the sample gas is comparatively low, the dilution ratio is reduced. But, even though this dilution ratio is small, the concentrations of $H_2$ and CO in the sample gas are small from the beginning. Accordingly, the combustion heat generated by their combustion will be small so that the promotion of combustion of HC products is also relatively small. Again, the influence of the water byproducts of the HC combustions is reduced, and the S/N ratio in the water meter is maintained so that a highly accurate measurement can be conducted.

The features of the present invention which are believed to be novel are set forth with particularity in the appended claims. The present invention, both as to its organization and manner of operation, together with further objects and advantages thereof, may best be understood by reference to the following description, taken in conjunction with the accompanying drawings.

DESCRIPTION OF THE PREFERRED EMBODIMENTS

The following description is provided to enable any person skilled in the gas analyzing field to make and use the invention and sets forth the best modes contemplated by the inventors of carrying out their invention. Various modifications, however, will remain readily apparent to those skilled in these arts, since the generic principles of the present invention have been defined herein specifically to provide a relatively economical and highly accurate hydrogen gas analyzer.

Figure 1:
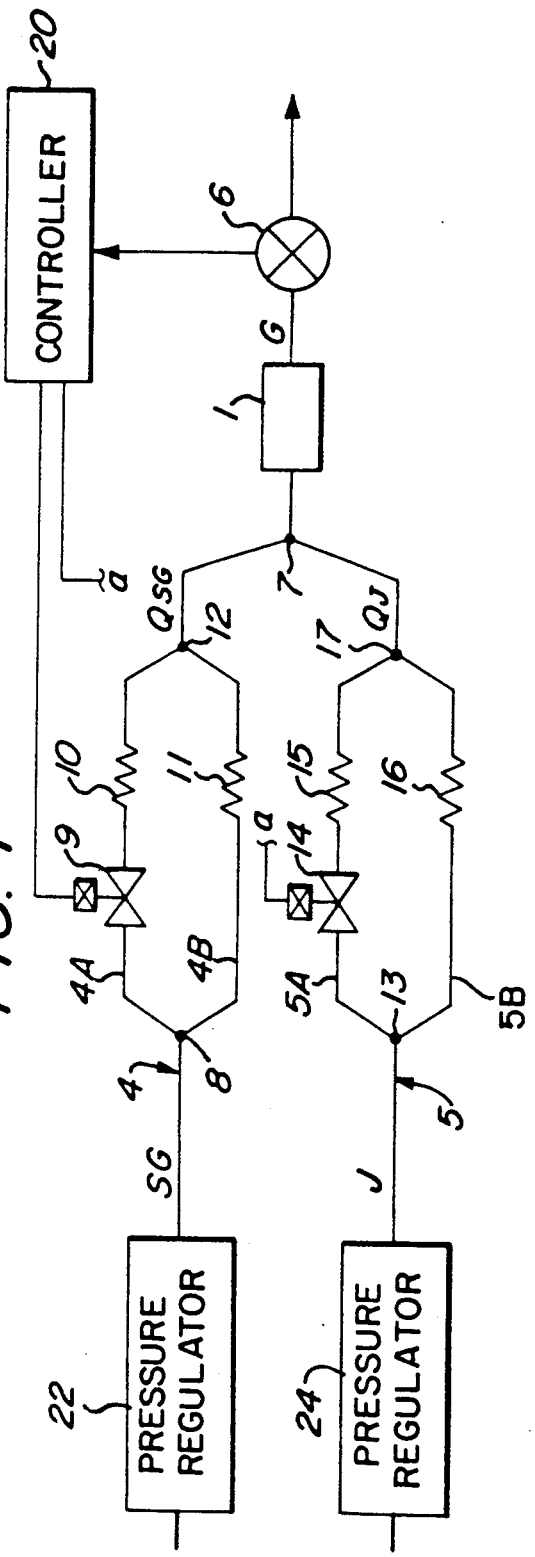
FIG. 1 is a schematic block diagram of a hydrogen gas analyzer system according to a preferred embodiment of the present invention.
Figure 2:
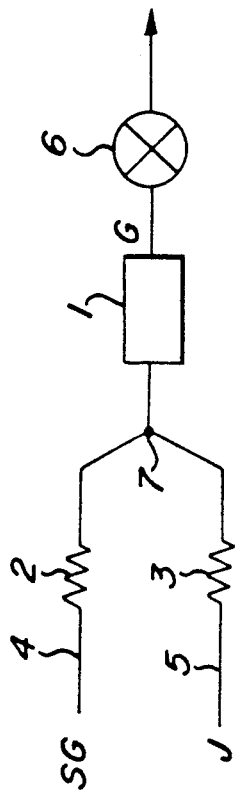
FIG. 2 is a schematic block diagram showing a conventional hydrogen gas analyzer.

In referring to the component parts in the drawings of FIGS. 1 and 2, common parts will be labelled with common reference numbers.

Referring to FIG. 1, a sample gas, SG, is delivered through a sample gas supply passage 4 to a junction point 8. A pair of passageways are branched from the junction point 8 as passageways 4A and 4B. The passageway 4A contains an on/off valve 9 such as an electromagnetic valve, which can be controlled by a controller 20. Downstream of the on/off valve 9 is a restrictive capillary section 10 that is utilized to regulate the flow rate. The parallel branched passageway 4B also carries a restrictive capillary 11 for use in regulation of the flow rate. Each of these parallel branched passageways 4A and 4B are rejoined at a junction point 12 on the downstream side of their respective restrictor capillaries 10 and 11.

An additive or assistant fuel gas J can be introduced through a fuel gas supply passage 5 to a junction point 13. Again, a pair of branched passageways 5A and 5B extend from the junction point. Passageway 5A also contains an on/off valve 14, such as an electromagnetic valve, that is also controlled by the controller 20. Again, a restrictive capillary 15, that is used in the regulation of the flow rate in series, is provided downstream of the on/off valve 14. The other passageway 5B has a restrictive capillary 16. The branched passageways 5A and 5B are joined at a junction point 17 on the downstream side of the respective capillaries 15 and 16.

The restrictive capillaries 10, 11 and 15, 16 are set to provide the same flow rate characteristics so that the quantity of gas, passing through each of the respective capillaries 10, 11 and 15, 16, will be balanced to be equal to each other, for example, one liter per minute. In addition, the gas pressure for the sample gas supply passageway 4 on the upstream side of the junction point 8 and the additive fuel gas supply passageway 5 on the upstream side of the junction point 13 are both set to be at a constant pressure, respectively, by the pressure regulators 22 and 24. Thus, by balancing the delivery system of both the sample gas and the additive fuel gas, plus the flow characteristics of each of the parallel passageways, it is possible to adjust the conditions to optimize the measurement of hydrogen, regardless of its particular concentration level in the sample gas.

In measuring the concentration of $H_2$ in a sample gas SG, when the concentration of $H_2$ in the sample gas is comparatively high, the on/off valve 9 on the side of the sample gas supply passageway 4 can be closed. At the same time, the on/off valve 14 on the side of the additive fuel gas supply passageway 5 can be opened. As a result, the ratio of the flow rate $Q_{SG}$ of the sample gas SG at the confluential point 12 in the sample gas supply passageway 4 to that of $Q_J$ of the additive fuel gas J at the confluential point 17 in the additive fuel gas supply passageway 5 can, for example, be on the ratio of 1:2. Thus, the sample gas, SG, supplied to the catalytic combustion tank 1 can be diluted with the additive fuel gas J to reduce the concentration thereof until it represents one-third of the input to the catalytic tank 1. As a result, the concentrations of $H_2$ and CO in the sample gas SG are reduced. Thus, even if they are burned, the combustion heat is reduced, and also the temperature rise of the catalytic tank 1 will be reduced so that the combustion of HC components is minimized. As a result, the adverse influence of the HC components in the measurement of the concentration of $H_2$ can be minimized. Since the S/N ratio in the water meter 6 is not reduced, the sensitivity of the measurement will also not be reduced, and a highly accurate measurement can be accomplished.

When the concentration of $H_2$ in the sample gas SG is comparatively low, then the on/off valve 9 is opened and, at the same time, the on/off valve 14 is closed. This can be controlled by the controller 20 that is monitoring the water meter 6 output signals. In this case, the ratio of the flow rate $Q_{SG}$ to the flow rate $Q_J$ amounts to 2:1. Thus, the sample gas SG supplied to the catalytic tank 1 is diluted with the additive fuel gas J to reduce the concentration thereof, so that it represents two-thirds of the flow rate supplied to the catalytic tank 1. In this case, the dilution ratio of the sample gas SG with the additive fuel gas J is smaller than that in the above circumstance of having a comparatively high $H_2$ concentration. However, the concentrations of $H_2$ and CO in the sample gas are small in most measurements, and thus the combustion of HC will not be promoted, and the S/N ratio on the water meter will not be reduced. Accordingly, the sensitivity measurement is also not reduced, and a highly accurate measurement can be conducted. As can be appreciated, in the preferred embodiment, the restrictive capillaries 10, 11 and 15, 16 are adapted to be equal to each other to provide correspondingly equal flow rate characteristics, so that the total gas quantity of the sample gas SG and the additive fuel gas J introduced into the catalytic tank 1 can be made constant, regardless of the concentration of $H_2$ in the sample gas SG. Thus, the quantity of the gases supplied to the water meter 6 will not fluctuate and the quantitative determination of $H_2O$ in the water meter 6 can be accurately conducted. In the preferred embodiment, the above-described on/off operation of the respective on/off valves 9 and 14 can be interlocked with the switchover of the measurement ranges in the water meter 6. This can be monitored and effectuated through the controller 20. Thus, with a higher concentration range of $H_2$, the on/off valve 9 will beclosed and the on/off valve 14 will be opened and vice versa, with a lower concentration of $H_2$.

While the above features of the present invention adequately teach the invention to a person of ordinary skill in this field, it can be readily appreciated that it would be possible to deviate from the above embodiments of the present invention such as, for example, scaling the flow rates in the passageways. Accordingly, it should be understood that the invention is not to be limited by the specific embodiment, but only by the spirit and scope of the appended claims.

What is claimed is:

1. In a hydrogen gas analyzer system for determining the concentration of hydrogen gas in a sample gas that is combusted in a combustion chamber with an additive fuel and analyzed with an analyzing means, the improvement comprising:
   a source of an additive fuel;
   means for receiving a sample gas;
   first means for delivering the additive fuel to the combustion chamber, including at least a pair of first passageways of predetermined flow rates;
   a second means for delivering the sample gas from the receiving means to the combustion chamber, including at least a pair of second passageways of predetermined flow rates, and
   means for controlling the flow rates of the first passageways and the second passageways, whereby when the concentration of hydrogen in the sample is high the flow rate of the second means is reduced, and when concentration of the hydrogen in the sample is relatively low the flow rate of the first means is reduced.

2. The gas analyzer system of claim 1 wherein the respective pair of passageways in each of the first and second means are connected in parallel.

3. The gas analyzer system of claim 1 wherein a shutoff valve is mounted in a passageway in each of the first and second means.

4. The gas analyzer system of claim 1 wherein each passageway includes a restrictor to control flow rate.

5. The gas analyzer system of claim 1 further including means for measuring the concentration of hydrogen gas and a controller responsive to the measured concentration of hydrogen gas for providing a signal to regulate the means for controlling.

6. The gas analyzer system of claim 1 wherein the first and second means provides four parallel passageways connected to the combustion chamber and shutoff valves are mounted in two of the passageways.

7. In a hydrogen gas analyzer system for determining the concentration of hydrogen gas in a sample gas that is combusted in a combustion chamber with an additive fuel and analyzed with an analyzing means, the improvement comprising:
   a source of an additive fuel;
   means for receiving a sample gas;
   first means for delivering the additive fuel to the combustion chamber, including at least a pair of first passageways of predetermined flow rates;
   a second means for delivering the sample gas from the receiving means to the combustion chamber, including at least a pair of second passageways of predetermined flow rates;
   shutoff valves positioned in at least one passageway of each of the first and second passageways;
   means, connected to the combustion chamber, for measuring the concentration of hydrogen gas, and providing a representative signal;
   means for controlling the flow rates of the first passageways and the second passageways by activating the shutoff valves in response to the representative signal, whereby when the concentration of hydrogen in the sample is high the flow rate of the second means is reduced, and when concentration of the hydrogen in the sample is relatively low the flow rate of the first means is reduced.

8. The gas analyzer system of claim 7 further including a pressure regulator connected to respectively the first and second means.

9. The gas analyzer system of claim 7 wherein each passageway is mounted in parallel fluidic connection between the respective additive fuel and sample gas and contains a restrictor to balance the flow rates to a predetermined flow rate for each passageway.

10. The gas analyzer system of claim 7 wherein the first and second means provides four parallel passageways connected to the combustion chamber and shutoff valves are mounted in two of the passageways.

11. In a hydrogen gas analyzer system for determining the concentration of hydrogen gas in a sample gas that is combusted in a combustion chamber with an additive fuel and analyzed with an analyzing means, the improvement comprising:
    a source of an additive fuel;
    means for receiving a sample gas;
    pressure regulator means for establishing a constant pressure level for both the additive fuel and the sample gas;
    first means for delivering the additive fuel to the combustion chamber, including at least a pair of first passageways of predetermined flow rates providing parallel flow passageways;
    a second means for delivering the sample gas from the receiving means to the combustion chamber, including at least a pair of second passageways of predetermined flow rates providing parallel flow passageways;
    shutoff valves positioned in at least one passageway of each of the first and second passageways;
    means, connected to the combustion chamber, for measuring the concentration of hydrogen gas, and providing a representative signal;
    means for controlling the flow rates of the first passageways and the second passageways by activating the shutoff valves in response to the representative signal, whereby when the concentration of hydrogen in the sample is high the flow rate of the second means is reduced, and when concentration of the hydrogen in the sample is relatively low the flow rate of the first means is reduced.

12. The gas analyzer system of claim 11 wherein each passageway includes a restrictor to control flow rate.

* * * * *